United States Patent [19]

Parissenti et al.

[11] Patent Number: 4,843,643
[45] Date of Patent: Jul. 4, 1989

[54] PROTECTIVE VISOR, PARTICULARLY FOR DENTISTS

[75] Inventors: Stefano Parissenti; Lino Parissenti, both of Agordo, Italy

[73] Assignee: M.P.A. Meccanica Plastica Agordina S.p.A., Agordo, Italy

[21] Appl. No.: 107,738

[22] Filed: Oct. 13, 1987

[30] Foreign Application Priority Data

Apr. 3, 1987 [IT] Italy ................................ 41570 A/87

[51] Int. Cl.⁴ .............................................. A61F 9/04
[52] U.S. Cl. .................................................. 2/13; 2/9; 351/158; 128/857
[58] Field of Search ................. 2/13, 9, 435, 427, 206; 351/158, 57, 58; 128/139, 201.12

[56] References Cited

U.S. PATENT DOCUMENTS

| 3,183,523 | 5/1965 | Harrison | 2/13 |
| 3,298,032 | 1/1967 | Sielisch | 2/13 |
| 3,392,463 | 7/1968 | Hachigian | 2/13 X |
| 3,991,753 | 11/1976 | Viesca | 2/9 X |
| 4,414,693 | 11/1983 | Brody | 2/435 |
| 4,701,965 | 10/1987 | Landis | 2/9 X |

FOREIGN PATENT DOCUMENTS 0513750 10/1939 United Kingdom ...................... 2/9

Primary Examiner—Peter Nerbun
Attorney, Agent, or Firm—Guido Modiano; Albert Josif

[57] ABSTRACT

Protective visor, particularly for dentists, composed of a shield supported by a supporting element having bar elements connectable to the rods of a pair of spectacles or the like.

8 Claims, 1 Drawing Sheet

PROTECTIVE VISOR, PARTICULARLY FOR DENTISTS

BACKGROUND OF THE INVENTION

The present invention relates to a protective visor particularly for dentists.

The risks of infection to which dentists may be subject in treating both patients who are healthy carriers of the AIDS virus and those affected thereby are generally known.

In fact, since dentists have to operate with their face proximate to the mouth of the patients, during the drilling of teeth, extractions, etc., they may be sprayed with blood, which is the most effective means of spread of the disease.

SUMMARY OF THE INVENTION

From what has been described, the aim of the present invention is therefore to devise a device for protecting the face of dentists during dental surgery.

An important object is to provide a device which is in particular easily applicable to any type of spectacles or of supporting frames.

Another object is to devise a visor which can be an integral part of a pair of spectacles or of a supporting frame.

Yet another object is to provide a visor which can be adapted to the size of all types of faces.

Not least object is to provide a device having a modest cost, which can be manufactured with ordinary plants.

This aim, these objects, and others which will become apparent hereinafter, are achieved by a protective visor, particularly for dentists, according to the appended independent claims.

BRIEF DESCRIPTION OF THE DRAWINGS

Further characteristics and advantages of the invention will become apparent from the detailed description of two embodiments of the visor, illustrated only by way of nonlimitative example in the accompanying drawings, wherein.

DESCRIPTION OF THE PREFERRED EMBODIMENTS

Figure 1:
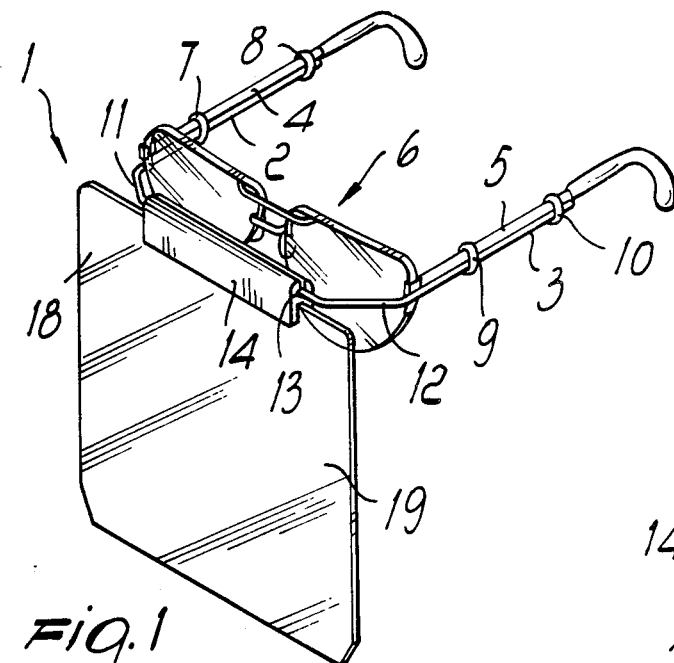
FIG. 1 is a perspective view of a first embodiment of the invention.
Figure 2:
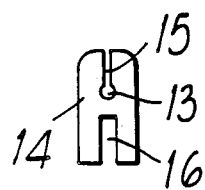
FIG. 2 is a lateral enlarged view of a monolithic supporting element for the shield.

With reference to the above described FIG. 1, the visor in its first embodiment is generally indicated by the reference numeral 1, and comprises two small metallic bars, respectively 2 and 3, each L-shaped and associated by means of an end portion thereof with one of the two temples 4 and 5 of a pair of spectacles 6.

The coupling is achieved by means of rings of an elastic material, respectively 7, 8 9 and 10, each whereof embraces a portion of a bar and of a temple arranged mutually side by side.

The two bars thus associated with the spectacles are provided with two ends 11 and 12 in front of said spectacles and parallel thereto, so that each is insertable in the opposite end of a hole 13 which longitudinally traverses a monolithic cross supporting member, essentially parallelepipedal in shape.

Said monolithic cross member 14 is also longitudinally traversed by two vertical millings of grooves, respectively 15 and 16, one whereof extends in transverse cross section from the hole 13 to the upper surface, the other one extending, again in transverse cross section, from a narrow central portion 17 to a lower surface.

The milling 16 is the support and insertion seat for an upper portion 18 of a rectangular shield or screen 19 in transparent material and having antifogging surfaces.

The milling 15 is intended to allow a certain transverse elasticity to the monolithic element 14 so as to provide both the friction for the rotation thereof about the center of the hole 13 and the interchangeability of the shield 19.

The visor thus described can be adapted to spectacles of all widths, since it is sufficient for this purpose to insert more or less deeply the ends 11 and 12 in the hole 13.

Said structure is furthermore adaptable to all types of nose, since the distance between the shield 19 and the spectacles can be adjusted as required by sliding the small bars parallel to the temples.

Figure 3:
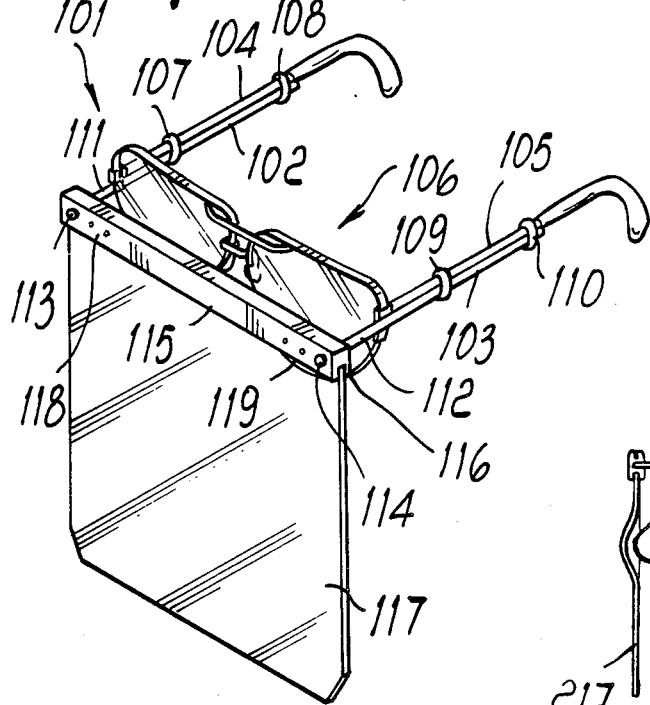
FIG. 3 is a perspective view of a second embodiment of the invention.

A second embodiment, illustrated in FIG. 3, is now generally indicated by the reference numeral 101, and comprises two small rectilinear bars 102 and 103, associated with the rods 104 and 105 of a pair of spectacles 106 by means of elastic rings, now indicated by 107, 108, 109 and 110, so that an end thereof protrudes in front of said spectacles 106.

Each of the protruding ends, respectively indicated by 111 and 112, is associated by means of small bolts 113 and 114 to a parallelepipedal monolithic element 115 provided with a vertical lower milling 116 which is the seat for a rectangular shield 117.

The monolithic element is provided with two series of holes 118 and 119 to allow various positions of association with the bars 102 and 103 so as to adapt the device to any type of spectacles.

In this case the shield 117 cannot be caused to swivel between a horizontal resting position and a vertical protecting position.

In other embodiments, the previously described devices, besides being applicable to spectacles or to lensless supporting frames for dentists with no eyesight impairment, can be an integral part of the structure of the spectacles or of the frame.

Figure 4:
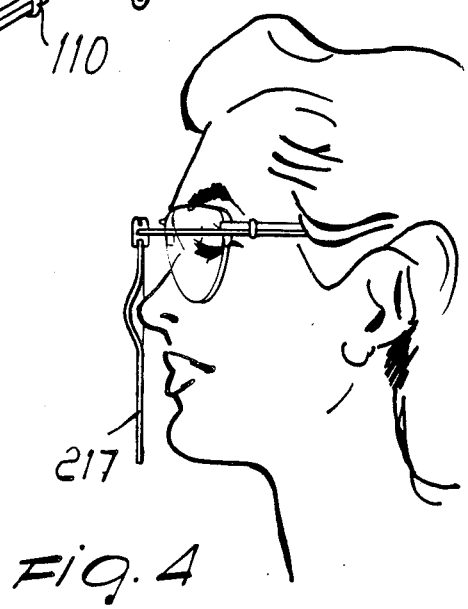
FIG. 4 is a lateral view in reduced scale of an embodiment showing a shield that has an anatomically shaped section.

Moreover, as shown in FIG. 4 the shape of the shield 217 may be defined in a particular or anatomical manner and can be associated with any supporting frame.

From what has been previously described, it is apparent that the invention achieves the intended aim and objects, since the protection of the face of dentists has been achieved with a device which is easily applicable to any type of spectacles or supporting frame and is furthermore adaptable to the dimensions of all faces.

The invention thus conceived is susceptible to numerous modifications and variations, all of which are within the scope of the inventive concept.

Moreover, all the details may be replaced with other technically equivalent elements.

In practice, the materials employed, as well as the dimensions, may be any according to the requirements.

We claim:

1. An adjustable protective visor, particularly suitable for dentists during dental surgery, adapted for use with a pair of spectacles or a like optical appliance, comprising:
- a shield of substantially transparent material positionable in front of a wearer's face to cover the eyes and the region of the nose and the mouth at a distance therefrom permitting free breathing to the wearer, said shield having an upper edge;
- means for supporting said shield in a selected position with respect to the wearer's face;
- means for removably associating said supporting means with a pair of conventional spectacles; wherein said supporting means comprises a pair of spaced apart bar elements positionable on each side of the wearer's head and a cross supporting member extending transversely to said bar elements, said bar elements being substantially L-shaped with first opposing end portions which extend coaxially to each other and in alignment with said cross supporting member and second end portions which extend rearwardly of and perpendicularly to said first portions in a substantially parallel direction to the spectacle temples, said cross supporting member comprising a unitary elongate body having at least one longitudinal through hole extending between the free ends thereof, said first end portions of said bar elements being frictionally insertable in said free end of said longitudinal hole to connect said bar elements with said cross supporting member, said elongate body further having a first longitudinal groove for firmly engaging therein said shield along said upper edge thereof, and wherein said means for removably associating said supporting means with said pair of spectacles comprise for each bar element at least a pair of longitudinally spaced elastic rings which are frictionally engageable with both said bar element and a respective temple for firmly coupling them in a substantially side-by-side relationship, whereby fitting of said supporting member to any width of spectacle frame can be obtained by inserting at selected depth said second portions of said bar elements into said longitudinal hole of said cross supporting member and whereby adjustment of the distance of said shield from the wearer's face can be achieved by selectively shifting said bar elements with respect to the spectacle temples.

2. An adjustable protective visor according to claim 1, wherein the body of said cross supporting member has a substantially parallelepipedal shape with an upper face and a lower face, said longitudinal hole being formed substantially centrally of said body, said first longitudinal groove extending from said lower face upwardly of said body with the top thereof spaced from said longitudinal hole.

3. An adjustable protective visor according to claim 2, further comprising a second longitudinal groove extending from said upper face of said parallelepipedal body downwardly up to said longitudinal hole to render it transversly elastically deformable.

4. An adjustable protective visor according to claim 1, wherein said shield is arranged to be elastically removably insertable in said first longitudinal groove.

5. An adjustable protective visor according to claim 3, wherein said longitudinal hole defines a rotation axis for said second portions of said bar elements, whereby said elongate body is permitted to frictionally swivel with respect to said bar elements about said axis to adjust said shield in a selected angular relationship with respect to the wearer's face.

6. An adjustable protective visor according to claim 1, wherein said shield is provided with antifogging surfaces.

7. An adjustable protective visor according to claim 1, wherein said shield is a substantially planar sheet.

8. An adjustable protective visor according to claim 1, wherein said shield is an anatomically shaped sheet conformed to the wearer's face.

* * * * *